(12) United States Patent
Rump

(10) Patent No.: US 7,851,711 B2
(45) Date of Patent: Dec. 14, 2010

(54) ELECTRONIC SCALES AND METHOD FOR CONTROLLING FOOD INTAKE AND/OR THE AMOUNT OF CALORIES CONSUMED USING A SENSOR AND WEIGHT-CHECKING ROUTINE

(76) Inventor: Björn S. Rump, 22 chemin du Rossignol, CH-1253 Vandoeuvres (CH)

( * ) Notice: Subject to any disclaimer, the term of this patent is extended or adjusted under 35 U.S.C. 154(b) by 212 days.

(21) Appl. No.: 12/064,098

(22) PCT Filed: Jul. 28, 2006

(86) PCT No.: PCT/IB2006/002164

§ 371 (c)(1),
(2), (4) Date: Jul. 9, 2008

(87) PCT Pub. No.: WO2007/020501

PCT Pub. Date: Feb. 22, 2007

(65) Prior Publication Data

US 2009/0205874 A1     Aug. 20, 2009

(30) Foreign Application Priority Data

Aug. 16, 2005   (CH) .................................. 1339/05

(51) Int. Cl.
*G06F 19/00* (2006.01)
(52) U.S. Cl. ................................ 177/25.16; 128/921
(58) Field of Classification Search .............. 177/25.16; 128/921
See application file for complete search history.

(56) References Cited

U.S. PATENT DOCUMENTS

| | | | | |
|---|---|---|---|---|
| 4,321,674 A | * | 3/1982 | Krames et al. | 600/300 |
| 4,686,624 A | * | 8/1987 | Blum et al. | 346/20 |
| 4,891,756 A | * | 1/1990 | Williams, III | 708/132 |
| 4,911,256 A | * | 3/1990 | Attikiouzel | 177/25.16 |
| 5,033,561 A | * | 7/1991 | Hettinger | 177/25.16 |
| 5,388,043 A | * | 2/1995 | Hettinger | 600/300 |
| 6,040,531 A | * | 3/2000 | Miller-Kovach et al. | 177/25.16 |
| 6,856,938 B2 | * | 2/2005 | Kurtz | 702/173 |
| 6,953,342 B2 | * | 10/2005 | Bisogno | 434/127 |

(Continued)

FOREIGN PATENT DOCUMENTS

DE    41 25 210 A1    2/1993

(Continued)

*Primary Examiner*—Randy W Gibson
(74) *Attorney, Agent, or Firm*—Young & Thompson

(57) ABSTRACT

Electronic scales to efficiently control the amount of calories consumed include at least one weight or force sensor, a data processing unit having a memory unit, a control and input keyboard and a display device. The scales include an active bearing surface functionally connected to the weight or force sensor(s) and adapted to receive a plate of food or similar container, and the data processing unit is installed with a program which calculates the equivalent calorie value for each meal, in the form of liquid and/or solid food, based on the amount of weighed food and the stored or manually input weight-related calorie content of the meal, finally, the other food of a meal is added to the equivalent calorie content and a total value of calories of the daily consumed meal is calculated. The value is stored, displayed and/or printed out and the storage unit stores pre-programmed desired values.

19 Claims, 2 Drawing Sheets

U.S. PATENT DOCUMENTS

| | | | |
|---|---|---|---|
| 6,956,175 B1 * | 10/2005 | Daly et al. | 177/1 |
| 6,978,221 B1 * | 12/2005 | Rudy | 702/173 |
| 7,348,500 B2 * | 3/2008 | Zhou | 177/25.16 |
| 7,361,143 B2 * | 4/2008 | Kirchhoff et al. | 600/300 |
| 7,413,438 B2 * | 8/2008 | Bisogno | 434/127 |
| 2002/0124017 A1 * | 9/2002 | Mault | 707/509 |
| 2002/0137990 A1 * | 9/2002 | Cardoso | 600/300 |
| 2003/0159857 A1 | 8/2003 | Lin et al. | |
| 2004/0118618 A1 * | 6/2004 | Davidson et al. | 177/25.13 |
| 2005/0184148 A1 * | 8/2005 | Perlman | 235/383 |
| 2007/0050058 A1 * | 3/2007 | Zuziak et al. | 700/90 |
| 2010/0038149 A1 * | 2/2010 | Corel | 177/25.16 |

FOREIGN PATENT DOCUMENTS

| | | |
|---|---|---|
| DE | 299 24 679 U1 | 10/2004 |
| GB | 2 317 961 A | 4/1998 |
| WO | 02/25228 A2 | 3/2002 |

* cited by examiner

ELECTRONIC SCALES AND METHOD FOR CONTROLLING FOOD INTAKE AND/OR THE AMOUNT OF CALORIES CONSUMED USING A SENSOR AND WEIGHT-CHECKING ROUTINE

This invention relates to the area of diet monitoring, especially equipment and devices available for this purpose.

The invention includes electronic scales for efficient monitoring of the number of calories consumed, and a process for monitoring the food intake of an individual.

Numerous programs and methods for reducing body weight are known, whether for cosmetic, general health or therapeutic reasons.

Many of these known programs and methods make it possible in fact to reduce body weight during their active application phase. This takes place in most cases by reducing calorie intake.

Monitoring of such a diet is based on detailed weighing or estimation of the weight of all foods during and between mealtimes, computation of the corresponding calories by means of a calorie table, and entry of all computed amounts into a daily, weekly and monthly table.

But practice shows that adherence to this systematic monitoring is only short-term in most diet candidates or extends in the best case only over a period of several months.

The explanation of this lies in large part in the tediousness of the numerous process steps, the required time expenditure, the absence of a systematic and automated monitoring procedure, efficient alteration of eating habits, the accessories which are impractical to use, and the disruption of the comfort of the candidate.

The object of this invention is to overcome the aforementioned defects.

In this regard the subject matter of the invention is electronic scales for efficient monitoring of the number of calories consumed, with at least one weight sensor or force sensor, a data processing unit with memory means, a control and input keyboard and a display device.

These scales are characterized in that they have an active bearing surface which is functionally connected to the weight or force sensor(s) and which is adapted to holding a dinner plate or similar vessel, that the data processing unit is equipped with a program which for any dish, in the form of liquid and/or solid food, based on the weighed amount of food and the weight-referenced calorie content of this food which has been stored or a manually input, computes the calorie equivalence value, adds the latter to the calorie equivalence values of the other dishes of a meal and computes the total value of the calories of foods consumed daily, and stores, displays and/or prints out this value and that the memory means are suited to containing preprogrammed setpoints which are computed from the data inputs and measurements of a calibration period and are used as comparison or reference values during the period of calorie monitoring.

The invention relates to a process for monitoring the food intake of an individual within the framework of a diet and using the aforementioned electronic scales, characterized in that the process in terms of time consists of three successive phases, specifically a first calibration period of limited duration, a subsequent effective diet period, and finally a long-term stabilization period, during all three periods the daily calorie equivalence values of the foods consumed being computed by means of the electronic scales, by weighing the individual foods of each meal, computing the corresponding calories and adding up the latter for each day of these three periods, in the third period or stabilization period the efficiency or the correctness of the number of calories consumed daily being monitored by regularly determining the body weight by weighing, and if necessary being empirically corrected to maintain the desired body weight.

In the following description the invention is detailed using one embodiment, in conjunction with the attached schematic figures.

Figure 1A:
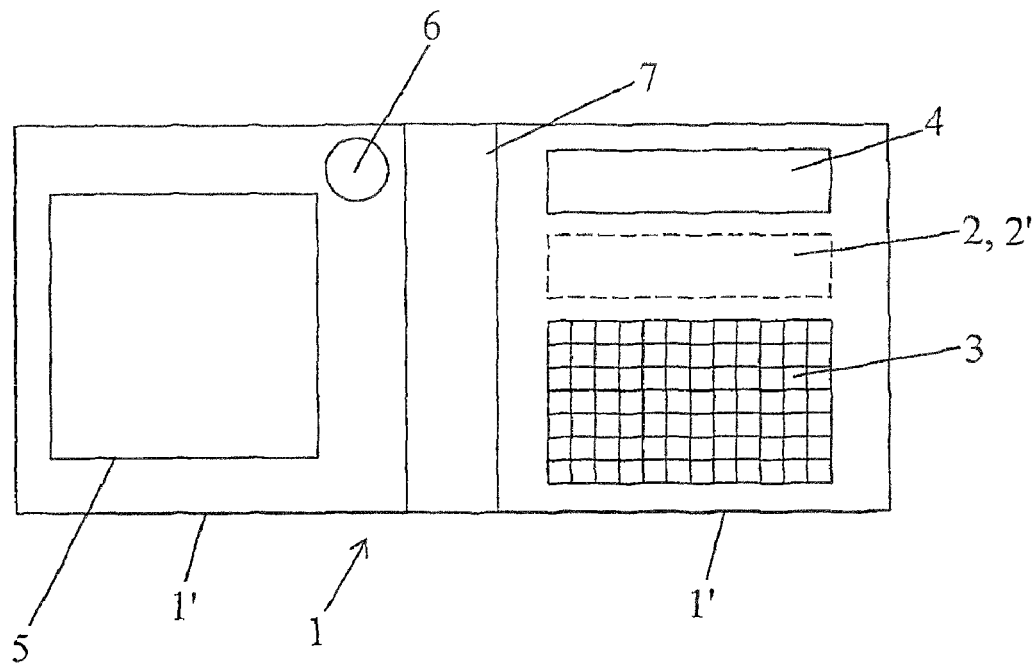
FIG. 1A shows a schematic top view of scales as claimed in the invention in the position of use.

As follows from the attached FIGS. 1A and 1B, the scales 1 are equipped with at least one weight or force sensor, a data processing unit 2 with memory means 2', a control and input keyboard 3 and a display device 4.

It is provided as claimed in the invention that the scales have an active bearing surface 5 which is functionally connected to the weight or force sensor(s) and which is adapted to holding a dinner plate or similar vessel, that the data processing unit 2 is equipped with a program which for any dish, in the form of liquid and/or solid food, based on the weighed amount of food and the weight-referenced calorie content of this food which has been stored or a manually input, computes the calorie equivalence value, adds the latter to the calorie equivalence values of the other dishes of a meal and computes the total value of the calories of foods consumed daily and stores, displays and/or prints out this value and that the memory means 2' are suited to containing preprogrammed setpoints which are computed from the data inputs and measurements of a calibration period and are used as comparison or reference values during the period of calorie monitoring.

The user thus has a compact and easily managed device which greatly facilitates accurate monitoring of his diet.

So that fault-free and precise functioning of the scales 1 can be ensured, it is provided that the bearing surface 5 and the weight or force sensors assigned to it are designed such that plates of different sizes and shapes can be accurately weighed and that the program contains a routine which checks during each weight measurement phase that each weight or force sensor is loaded and is delivering a correct measurement signal which contributes to an effective measurement result.

In order to be able to evaluate the liquids and beverages consumed at meals in addition in foods in solid form, the scales 1 preferably contain at least one second active bearing surface 6 which separately from the first bearing surface 5 is equipped with its own weight or force sensor(s) and is functionally connected thereto and is suited for holding drinking vessels or containers, such as glasses or cups, at least one second measurement signal being delivered therefrom.

So that the scales 1 can be easily used, carried and put away in practice, their overall structure is essentially flat and thin (and equivalent for example to that of a place mat), with a bearing surface 5 for the plate and a bearing surface 6 for a drinking vessel, the programming and control keyboard 3 and the display device 4 which consists for example of liquid crystal diodes being arranged pushed to the side, and thus even when a plate and/or a drinking vessel is present, being visible or reachable.

Figure 1B:
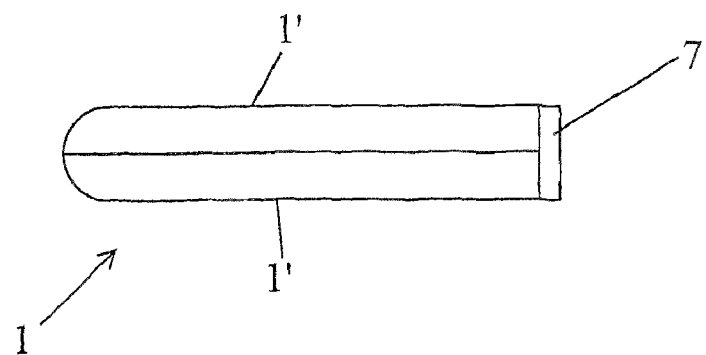
FIG. 1B shows a side view of the scales of FIG. 1A in the folded state.
Figure 2:
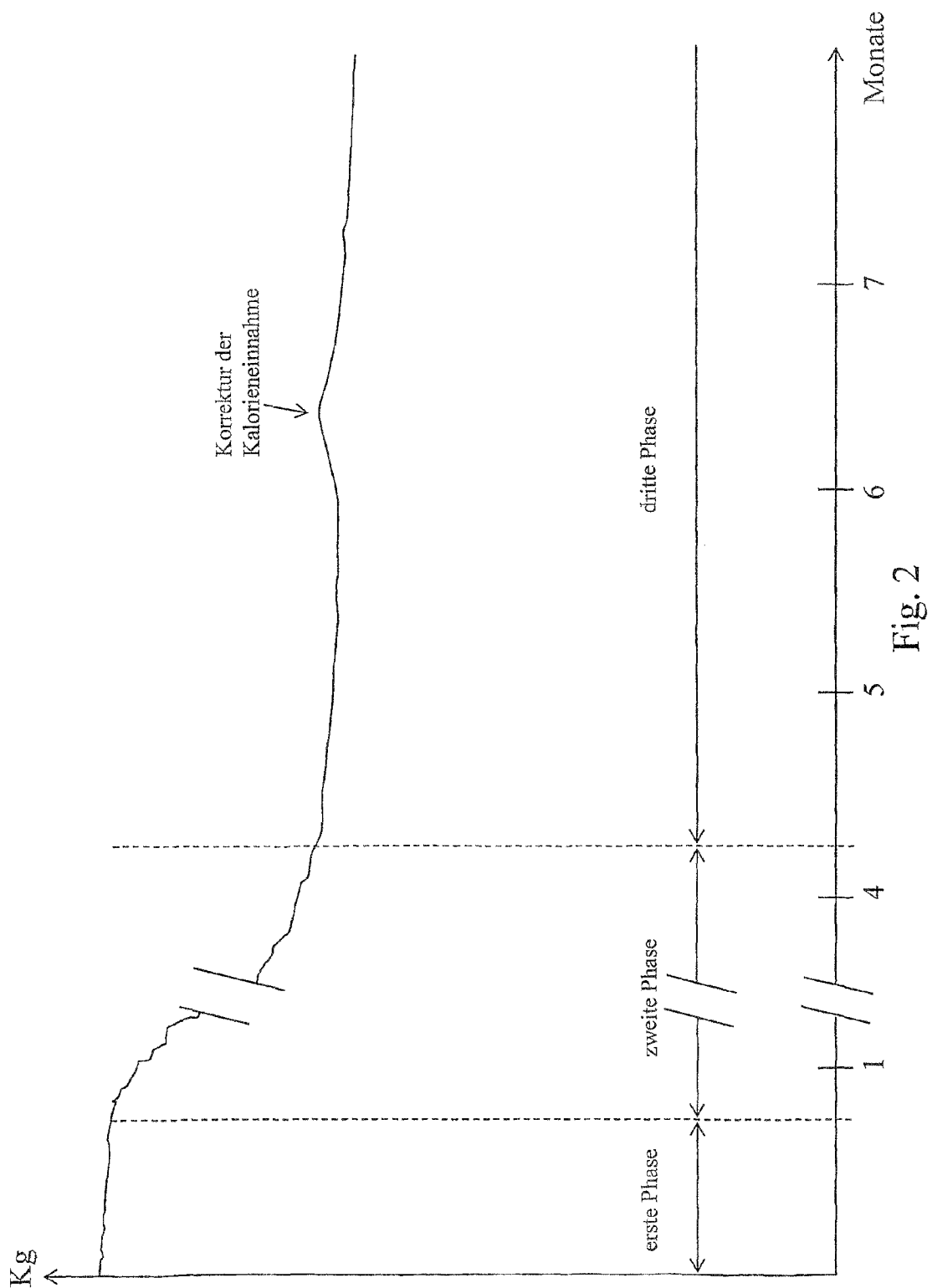
FIG. 2 is a schematic time diagram which for example shows the change of the body weight of an individual who is using the process as claimed in the invention over time.

As FIGS. 1A and 1B show, the scales can consist for example of two flat jackets 1' which are hinged to one another via a hinge part 7, and the scales can thus be folded together when not in use and/or for transport.

The jackets 1' which surround the functional components of the scales 1 and which determine the outer form of its overall structure, consist preferably of a stiff material, such as a high-grade steel sheet or plastic, which is suitable for cleaning after contact with food.

Preferably the scales also contain blocking means which make it possible to rigidly lock the bearing surface 5 for the plate, and optionally the bearing surface 6 for the drinking vessel, outside of a measurement and computation phase, in a given position and/or blocks and prevents any data transfer as the measurement signal to the data processing unit 2, thus the movements necessary for eating and drinking can be carried out safely and without disruption.

According to one advantageous feature of the invention, the memory means 2' contain a programmable calorie equivalence table which can be interrogated and supplemented, and which can be interrogated and supplemented by data input via the keyboard 3, and interrogation can take place by input of only some of the letters of the name of the pertinent dish/food and the value which has been interrogated at the time is automatically used by the data processing unit 2 as a multiplication factor for computing the calorie value of a weighed dish/food.

For example, it can be provided that when the user inputs the letters "BR", the display means 4 display the word "BROT [bread]" and other words which start with "BR", and the correct word must then only be validated.

Furthermore it can be provided that the calorie equivalence table which can be interrogated, for individuals who are suffering from a disease and thus are to consume specifically on a daily basis at least or at most values of an element or molecule, contains the specific content of the critical proportions of the given food list and its daily total is likewise computed.

These critical proportions can be input by the keyboard (for example apple juice×g glucoside/100 g liquid in the case of an individual who is suffering from acute diabetes).

It is also provided that the program, upon the corresponding control by the keyboard 3, measures and stores the empty weight of the plate and/or the drinking vessel, i.e. determines the tare weight, and afterwards computes and stores the net calorie value of each dish/food of a meal in place, the total calorie value of each meal and the cumulative calorie value of the different meals of a day, optionally also the plus/minus difference from a daily calorie setpoint which has been computed beforehand or input beforehand being computed and displayed.

The stored values, optionally supplemented by a date and/or time indication and/or by data which have been input manually via the keyboard 3, can be transmitted from the corresponding integrated or separate connected means to a data medium, such as for example a sheet of paper, an electronic data card, a solid state memory or the like.

Furthermore the scales can likewise have means for visual or audible reproduction of reports, especially of result reports, comments, warnings, deviations from the stored diet program and the like.

The invention also relates to a process for monitoring the food intake of an individual within the framework of a diet and using electronic scales as described above. This process in terms of time consists of three successive phases, specifically a first calibration period of limited duration, a subsequent effective diet period and finally a long-term stabilization period, during all three periods the daily calorie equivalence values of the foods consumed being computed by means of the electronic scales 1, by weighing the individual foods of each meal, computing the corresponding calories and adding up the latter for each day of these three periods, in the third period or stabilization period the efficiency or the correctness of the number of calories consumed daily being monitored by regularly determining the body weight by weighing, and if necessary being empirically corrected to maintain the desired body weight.

As claimed in the invention, the values with respect to the daily calorie intake of the individual during the first phase are used as the basis for computing reference values for the second and third phase, in the second and third phase a deviation of the effective daily calorie intake value from the corresponding reference value computed beforehand being displayed and/or reported.

Advantageously the reference value of the second phase constitutes 0.75 to 0.90 of the daily average of the first phase and the reference value of the third phase constitutes 0.95 to 1.15 of the daily average of the second phase, the reference value of the third phase optionally being empirically adjustable in conjunction with the prevailing weight change of the individual.

The first phase is used to determine the average daily calorie intake before the diet. The second phase ends with reaching the desired weight of the individual. The third phase is used to allow the newly reduced food intake to become the actual eating habit.

It can furthermore be provided that for specific diet programs, in addition to the total calorie value of the food consumed, by expanding the stored calorie values of the individual foods, by additional storage of the content of proteins, carbohydrates, fat or other foods which are to be limited for medical reasons can be measured and thus can be kept within the desired limits.

The different subject matters and features of the invention will now be detailed below using one example.

The invention consists of three parts, specifically of a process (or method), a device (electronic scales) and a control, monitoring and communications program which is executed by the device and which is used for its operation.

The method in itself consists in first determining for roughly two weeks the daily amount of food of the individual who intends to permanently reduce his body weight, and the average daily calorie value on the basis of the foods and beverages consumed during meals and between meals.

As soon as this calorie value has been determined, it is reduced by roughly 10-25% and the affected individual commits himself to being limited to the corresponding amount of food. It is possible to adhere to this diet without major limitations, i.e. feelings of hunger. Conversely it is impossible to adhere to this limitation without correctly determining and knowing calories consumed.

The body weight of the individual is determined weekly by weighing and is recorded on a graph. The trend which is apparent on the graph is a very strong motivation for the individual to continue to maintain diet discipline.

If after a few months the desired body weight is reached, the most important phase of the program begins. The daily number of calories is increased by roughly 5% and their intake is monitored and maintained for months. The further development of the weight is determined by weighing weekly. If the weight changes in this time, it is easily possible—since daily consumption is known—to adapt it empirically up or down. The final objective is to learn eating habits which make the daily monitoring of consumption superfluous. The experience of many diet programs has shown that the desired weight reduction is quite possible, but that in almost all cases the feared, so-called yo-yo effects occurs, i.e. that the weight of the individual soon reaches the initial value again. This method is intended to make to path to permanent weight reduction as easy as possible for the individual who intends to lose weight by acquisition of other eating habits.

To facilitate adherence to the described method during meals the scales 1 as claimed in the invention are placed under the dinner plate.

These scales should be made such that they fit under a plate and that the weight display is stored by the computer 2 which is built into the scales 1, multiplied by the calorie factor of the food, and the number of calories which has been determined in this way is added to the daily total and displayed. This simplified process greatly facilitates the required intake monitoring, requires less discipline and since it can be carried out with little effort, can be used over a longer time during which it is possible to permanently alter eating habits, as mentioned.

The scales 1 have at least one bearing surface 5 which corresponds to the current diameter of the plate, is built to be as light as possible, and shows the result of weighing in "g" in a few seconds on a liquid crystal diode display screen 4. The scales are turned on by placing the plate on them and are set to zero (tare weight). After loading the plate with food the user with a numerical keypad 3 (0-9) types the calorie content of the food loaded onto the plate, which content is known to him, and presses the "Enter button". In the manner known to one skilled in the art, the microprocessor of the data processing unit 2 computes the calorie value of the food which has been loaded on the plate and displays it on the screen (display means 4). The result is added to the total by "Enter". When further amounts of food are added, the process is repeated accordingly. Before the start of consumption the scales are blocked so that the plate can remain lying on the scales and the food can be cut and eaten without the results being changed or influenced.

At the next meal the scales 1 can be activated by "Enter" without the previous number of calories (those of the last meal) being erased. The following meal, i.e. its calorie value, is then determined in the described manner. After the last meal of a day, by pushing the corresponding key, the daily total and if necessary the deviation from the desired setpoint will be displayed. This display has a pedagogical value, it rewards the discipline exercised or gives warning for excesses. The numbers of calories determined by the method can be maintained without especially great effort.

The practical execution of the scales 1 and the program is obvious to one skilled in the art with respect to his knowledge, the development of the necessary logistics likewise. It is obvious that the desired monitoring function can be implemented in different ways without deviating from the principle of simply adding up the number of calories.

For example, a calorie table memory can be added to the device. After the weighing process, in the conventional manner the first letters of the food are typed in. This process is completed as soon as the desired food name appears on the display. This process is also known to one skilled in the art.

Since beverages likewise contain calories, the scales can be additionally equipped with a weighing surface 6 for glasses or cups, which analogously allows the acquisition of the poured amount of liquid.

Since many individuals often eat not only at home, one version of the scales in a form as light and flat as possible is advantageous; this makes it possible to carry the device into a restaurant or to an engagement and to use it there.

The scales 1 can also be programmed such that the user must estimate the calorie value and compare it afterwards to the measured value. This property can allow a motivated user to learn to estimate the calorie value with relative accuracy; this allows him to abandon detailed monitoring with time.

The computation, control, and administration program in the scales 1 can have or can execute for example the following functions:
 a. Determination of the weight in place and its display
 b. Recording of the manually input calorie value Multiplication of the two first values and their display
 c. Storage of calorie equivalence values and computation after typing the first letters of the name of the food (for example ka—Kartoffel [potato]) of the foods in place.
 d. Adding the new calorie value to the previous one
 e. Display of the daily total
 f. Computation and display of values which simplify use and allow the user to monitor his discipline and motivate him to adhere to the program, for example by indicating the difference of the daily total from the setpoint.
 g. The builder of the device has the freedom to announce to the user the results and their total and possibly motivating remarks by an integrated or external printer.
 h. Computing and subtracting the number of calories of the foods not consumed.

Of course the invention is not limited to the described embodiments. Changes, for example in the embodiments of the different parts or replacement by technical equivalents, are possible at any time, if they remain within the framework of what is claimed.

The invention claimed is:

1. Electronic scales for efficient monitoring of the number of calories consumed, with at least one weight sensor or force sensor, a data processing unit with memory means, a control and input keyboard and a display device, the scales having an active bearing surface (5) which is functionally connected to the weight or force sensor(s) and which is adapted to holding a plate,
   wherein the data processing unit (2) is equipped with a program which for any dish, in the form of liquid and/or solid food, based on the weighed amount of food and the weight-referenced calorie content of this food which has been stored or a manually input, computes the calorie equivalence value, adds the latter to the calorie equivalence values of the other dishes of a meal and computes the total value of the calories of foods consumed daily, and stores, displays and/or prints out this value and that the memory means (2) are suited to containing preprogrammed setpoints which are computed from the data inputs and measurements of a calibration period and are used as comparison or reference values during the period of calorie monitoring,
   wherein the bearing surface (5) and the weight or force sensors assigned to it are designed such that plates of different sizes and shapes are accurately weighed, and
   wherein the program contains a routine which checks during each weight measurement phase that each weight or force sensor is loaded and is delivering a correct measurement signal which contributes to an effective measurement result.

2. Electronic scales as claimed in claim 1, wherein they contains at least one second active bearing surface (6) which separately from the first bearing surface (5) is equipped with its own weight or force sensor(s) and is functionally connected thereto and is suited for holding drinking vessels or containers, at least one second measurement signal being delivered therefrom.

3. Electronic scales as claimed in claim 2, wherein their overall structure is essentially flat and thin, with a bearing surface (5) for the plate and a bearing surface (6) for a drinking vessel, the programming and control keyboard (3) and the display device (4) being arranged pushed to the side, and thus even when a plate and/or a drinking vessel is present, being visible or reachable.

4. Electronic scales as claimed in claim 3, wherein the scales comprise two flat (jackets 1') which are hinged to one another via a hinge part (7), and the scales are foldable together when not in use and/or for transport.

5. Electronic scales as claimed in claim 1, wherein the memory means (2') contain a programmable calorie equivalence table interrogated and supplemented by data input via the keyboard, and interrogation by input of only some of the letters of the name of the pertinent dish/food and the value which has been interrogated at the time is automatically used by the data processing unit (2) as a multiplication factor for computing the calorie value of a weighed dish/food.

6. Electronic scales as claimed in claim 5, wherein the calorie equivalence table, for individuals who are suffering from a disease and thus are to consume specifically on a daily basis at least or at most values of an element or molecule, contains the specific content of the critical proportions of the given food list and its daily total is likewise computed.

7. Electronic scales as claimed in claim 1, wherein the program, upon the corresponding control by the keyboard (3), measures and stores the empty weight of the plate and/or of the drinking vessel and afterwards computes and stores the calorie value of each dish/food of a meal in place, the total calorie value of each meal and the cumulative calorie value of the different meals of a day, also the plus/minus difference from a daily calorie setpoint which has been computed beforehand or input beforehand being computed and displayed.

8. Electronic scales as claimed in claim 1, wherein the stored values, are transmittable from the corresponding integrated or separate connected means to a data medium.

9. Electronic scales as claimed in claim 1, wherein they likewise have means for visual or audible reproduction of reports, comments, warnings, deviations from the stored diet program.

10. Process for monitoring the food consumption of an individual within the framework of a diet and using electronic scales for efficient monitoring of the number of calories consumed, with at least one weight sensor or force sensor, a data processing unit with memory means, a control and input keyboard and a display device, the scales having an active bearing surface (5) which is functionally connected to the weight or force sensor(s) and which is adapted to holding a plate, the data processing unit (2) equipped with a program which for any dish, in the form of liquid and/or solid food, based on the weighed amount of food and the weight-referenced calorie content of this food which has been stored or a manually input, computes the calorie equivalence value, adds the latter to the calorie equivalence values of the other dishes of a meal and computes the total value of the calories of foods consumed daily, and stores, displays and/or prints out this value and that the memory means (2) are suited to containing preprogrammed setpoints which are computed from the data inputs and measurements of a calibration period and are used as comparison or reference values during the period of calorie monitoring, wherein the process in terms of time comprises three successive phases, specifically a first calibration period of limited duration, a subsequent effective diet period and finally a long-term stabilization period, during all three periods the daily calorie equivalence values of the foods consumed being computed by means of the electronic scales (1), by weighing the individual foods of each meal, computing the corresponding calories and adding up the latter for each day of these three periods, in the third period or stabilization period the efficiency or the correctness of the number of calories consumed daily being monitored by regularly determining the body weight by weighing, and if necessary being empirically corrected to maintain the desired body weight.

11. Process a claimed in claim 10, wherein the values with respect to daily calorie intake of the individual during the first phase are used as the basis for computing reference values for the second and third phase, in the second and third phase a deviation of the effective daily calorie intake value from the corresponding reference value computed beforehand being displayed and/or reported.

12. Process a claimed in claim 10, wherein the reference value of the second phase constitutes 0.75 to 0.90 of the daily average of the first phase and the reference value of the third phase constitutes 0.95 to 1.15 of the daily average of the second phase, the reference value of the third phase being empirically adjustable in conjunction with the prevailing weight change of the individual.

13. Process as claimed in claim 10, wherein the second phase ends with reaching the desired weight of the individual.

14. Process as claimed in claim 10, wherein for specific diet programs, in addition to the total calorie value of the food consumed, by expanding the stored calorie values of the individual foods, by additional storage of the content of proteins, carbohydrates, fat or other foods which are to be limited for medical reasons are measurable.

15. Process a claimed in claim 11, wherein the reference value of the second phase constitutes 0.75 to 0.90 of the daily average of the first phase and the reference value of the third phase constitutes 0.95 to 1.15 of the daily average of the second phase.

16. Process as claimed in claim 11, wherein the second phase ends with reaching the desired weight of the individual.

17. Process as claimed in claim 11, wherein for specific diet programs, in addition to the total calorie value of the food consumed, by expanding the stored calorie values of the individual foods, by additional storage of the content of proteins, carbohydrates, fat or other foods which are to be limited for medical reasons are measurable.

18. Electronic scales as claimed in claim 1, wherein the program, upon the corresponding control by the keyboard (3), measures and stores the empty weight of the plate and/or of the drinking vessel and afterwards computes and stores the calorie value of each dish/food of a meal in place, the total calorie value of each meal and the cumulative calorie value of the different meals of a day.

19. Process a claimed in claim 10, wherein the reference value of the second phase constitutes 0.75 to 0.90 of the daily average of the first phase and the reference value of the third phase constitutes 0.95 to 1.15 of the daily average of the second phase.

* * * * *